US 6,527,783 B1

(12) United States Patent
Ignon

(10) Patent No.: US 6,527,783 B1
(45) Date of Patent: Mar. 4, 2003

(54) MICRODERMABRASION AND SUCTION MASSAGE APPARATUS AND METHOD

(75) Inventor: Roger G. Ignon, Redondo Beach, CA (US)

(73) Assignee: Edge Systems Corporation, Signal Hill, CA (US)

(*) Notice: Subject to any disclaimer, the term of this patent is extended or adjusted under 35 U.S.C. 154(b) by 27 days.

(21) Appl. No.: 09/698,409

(22) Filed: Oct. 27, 2000

Related U.S. Application Data

(63) Continuation of application No. 09/540,945, filed on Mar. 31, 2000.

(51) Int. Cl.$^7$ ............................................. A61B 17/50
(52) U.S. Cl. ..................... 606/131; 604/289; 604/290; 451/87; 451/88
(58) Field of Search ................. 609/290; 606/13.1; 451/87, 88

(56) References Cited

U.S. PATENT DOCUMENTS

| | | | |
|---|---|---|---|
| 2,701,559 A | 2/1955 | Cooper | 128/2 |
| 2,712,823 A | 7/1955 | Kurtin | 128/303 |
| 2,867,214 A | 1/1959 | Wilson | 128/355 |
| 2,881,763 A | 4/1959 | Robbins | 128/355 |
| 2,921,585 A | 1/1960 | Schumann | 128/355 |
| 3,964,212 A | 6/1976 | Karden | 51/170 |
| 4,378,804 A | 4/1983 | Cortese, Jr. | 128/355 |
| 4,957,747 A | 9/1990 | Stiefel | 424/691 |
| 5,012,797 A | 5/1991 | Liang et al. | 128/24 A |
| 5,037,431 A | 8/1991 | Summers et al. | 606/131 |
| 5,037,432 A | 8/1991 | Molinari | 606/131 |
| 5,100,412 A | 3/1992 | Rosso | 606/131 |
| 5,207,034 A * | 5/1993 | Lynn | 451/88 |
| 5,207,234 A | 5/1993 | Rosso | 128/898 |
| 5,620,414 A * | 4/1997 | Campbell, Jr. | 604/150 |
| 5,800,446 A | 9/1998 | Banuchi | 606/131 |
| 5,810,842 A | 9/1998 | Di Fiore et al. | 606/131 |
| 5,954,730 A | 9/1999 | Bernabei | 606/131 |
| 5,971,999 A | 10/1999 | Naldoni | 606/131 |
| 6,019,749 A | 2/2000 | Fields et al. | 604/313 |
| 6,039,745 A | 3/2000 | Di Fiore et al. | 606/131 |
| 6,042,552 A | 3/2000 | Cornier | 600/562 |
| 6,080,165 A | 6/2000 | DeJacma | 606/131 |
| 6,120,512 A * | 9/2000 | Bernabei | 604/289 |
| 6,238,275 B1 * | 5/2001 | Metcalf et al. | 451/87 |
| 6,303,119 B1 * | 10/2001 | Weisgerber et al. | 424/443 |
| 2001/0023351 A1 * | 9/2001 | Eilers et al. | 606/131 |

* cited by examiner

Primary Examiner—Aaron J. Lewis
Assistant Examiner—Linh Truong
(74) Attorney, Agent, or Firm—Myers Dawes & Andras LLP

(57) ABSTRACT

Microdermabrasion and suction massage apparatus are included in a single unit and alternatively connectable through a mode switch to a source of vacuum. The microdermabrasion section of the unit includes a crystal pick up station operating with a venturi effect to draw crystals through a hole into an air stream. The size of the hole is variable to control crystal density. A bleed valve is provided to control crystal velocity without controlling crystal density, while a bypass valve is provided to control crystal density without controlling crystal velocity. In an associated method, a microdermabrasion procedure is performed on the skin of a patient at an operative site. The mode switch is operated to activate the suction massage apparatus within the unit. This step is followed by performing a suction massage procedure at the operative site in order to promote healing of the abraded skin. The unit can be back-flushed by connecting various portions of the unit to a pressurized output of the source of vacuum.

19 Claims, 4 Drawing Sheets

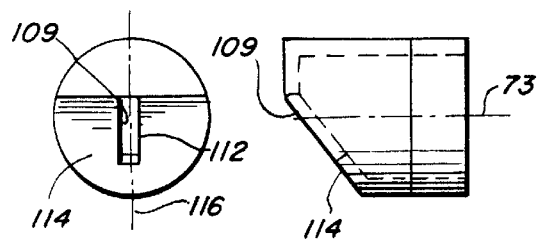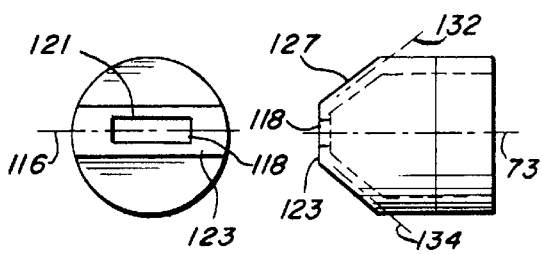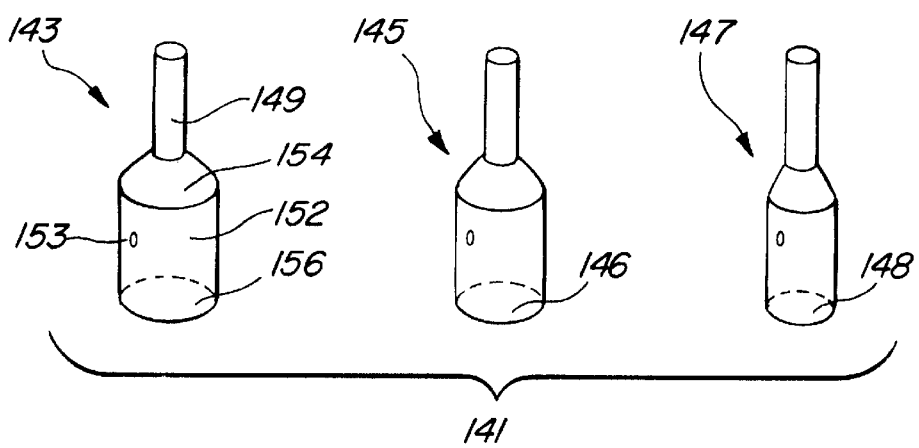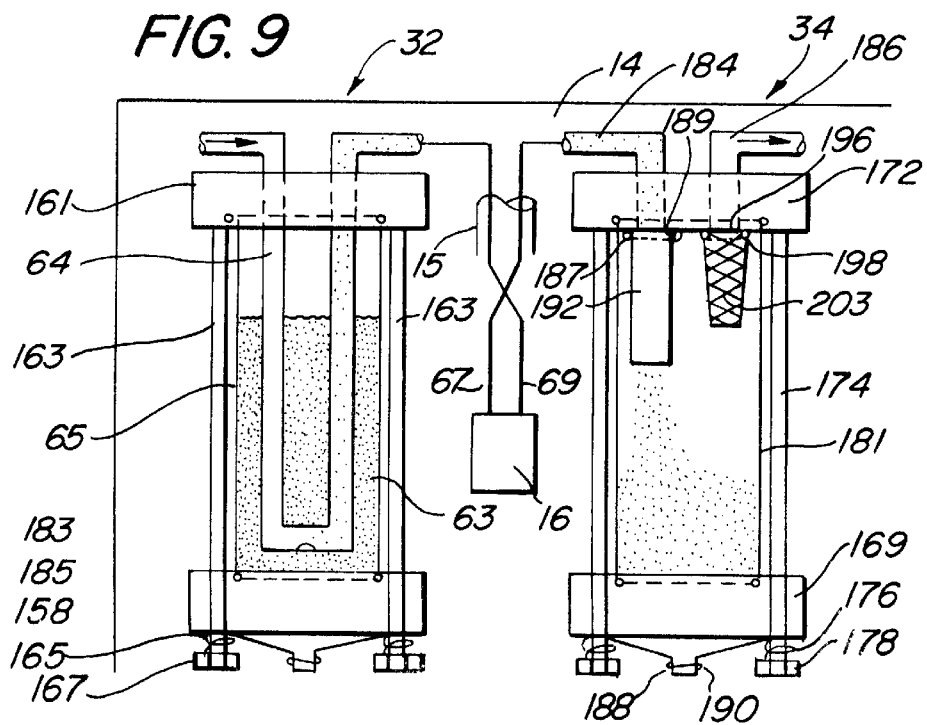

MICRODERMABRASION AND SUCTION MASSAGE APPARATUS AND METHOD

CROSS-REFERENCE TO RELATED APPLICATIONS

This is a continuation application claiming the priority of copending U.S. patent application Ser. No. 09/540,945 filed on Mar. 31, 2000 and entitled Microdermabrasion and Suction Massage Apparatus and Method.

BACKGROUND OF THE INVENTION

1. Field of the Invention

This invention relates generally to cosmetic apparatus and method used by a plastic surgeon, and more specifically to skin abrasion apparatus and cellulite massage apparatus.

2. Discussion of the Prior Art

Traditional dermabrasion has been used successfully to treat various types of scarring, for example scarring caused by acne. Wire brush and diamond fraise techniques have been used both, requiring local anesthesia and highly skilled surgical techniques. Bleeding has typically occurred requiring the surgeons and technicians to protect themselves from blood spray while performing the procedure. Postoperative complications have also been encountered.

In a new technique referred to as crystal microdermabrasion, aluminum oxide crystals flowing in an air stream have been applied to the skin. In this technique, there is less bleeding, fewer complications, better compliance, and no need for local anesthesia or high surgical skills. In the microdermabrasion technique, the velocity and density of crystals within the stream of air is related to the degree of abrasion which can occur over a fixed period of time. In the past, the crystal velocity has been controlled primarily by providing a bleed valve for the introduction of additional air into the stream of air. In a suction system this tends to slow the velocity of the operative air stream and thereby reduce the degree of abrasion. Although the velocity is decreased, the crystal density tends to stay the same with this approach.

Microdermabrasion handpieces have typically been formed with handles and caps which deine an abrasion chamber. The flow of crystals and the stream of air has been introduced into the abrasion chamber through a nozzle and along a supply path having a distal component. A return orifice communicating with the abrasion chamber has drawn the flow of crystals along a return path haaving proximal compnent. In the past, an abrasion window has been formed in the cap of the handpiece with the window being disposed only in the supply path of the crystal flow. In the past the window has been provided only with a circular configuration, These structural limitations have not tended to maximize the abrasive qualities of the stream.

A system for cellulite massage has been used by the same surgeons and technicians in an apparatus heretofore separate from the microdermabrasion apparatus. This procedure is, commonly referred to as endermologie massage, has had as its primary purpose the reformation of collagen fibers particularly in cellulite. Cellulite occurs as a combination of several factors which may be hormonal, circulatory, and nutritional. Inherent genetics also contribute to this condition where the skin tends to take an orange-peel texture. Nippling of the skin is relieved during this treatment by the applied suction massage. Congestion is alleviated by increasing oxygenation in the blood circulation to the tissue altered by cellulite. The procedure also increases exchanges with the connective tissue and boosts the metabolism rate allowing the body to dispose of toxins naturally. Stretching the collagen fibers and strengthening the elastic fibers make the surface of the skin smoother and firmer. This procedure, requiring a source of vacuuming has been of particular advantage not only in the treatment of cellulite, but also in post-operative liposuction care. In the after instance, post-operative endermologie treatments have maximized results and offered the additional advantage of keeping patients in communication with the practice and focusing on long-term goals. Particularly when combined with a dietary program and exercise, repeated small-volume liposuction with endermologie following each procedure, has shown significant results. contribute to this condition where the skin tends to take an orange-peel texture. Nippling of the skin is relieved during this treatment by the applied suction massage. Congestion is alleviated by increasing oxygenation in the blood circulation to the tissue altered by cellulite. The procedure also increases exchanges with the connective tissue and boosts the metabolism rate allowing the body to dispose of toxins naturally. Stretching the collagen fibers and strengthening the elastic fibers make of the surface of the skin become smoother and firmer. This procedure, requiring a source of vacuuming has been of particular advantage not only in the treatment of cellulite, but also in post-operative liposuction care. In the latter instance, post-operative endermologie treatments have maximized results and offered the additional advantage of keeping patients in communication with the practice and focusing on long-term goals. Particularly when combined with a dietary program and exercise, repeated small-volume liposuction with endermologie following each procedure, has shown significant results.

In the endermologie procedure, a source of vacuum is applied to a conduit terminating at an endermologie handpiece. The handpiece has typically been provided in the configuration of a cylinder having a single fixed diameter.

While these two apparatus, the microdermabrasion apparatus, and the endermologie apparatus, have commonly been provided as separate instruments, they nevertheless have been used by the same surgeons and technicians. More recently, it has been found that the microdermabrasion procedure can be facilitated by the use of an aspiration system to promote tissue blood supply and thereby facilitate fast healing and scar tissue repair. Under these circumstances, the aspiration or suction system associated with the endermologie apparatus has been found of value in the microdermabrasion procedure. Notwithstanding this advantageous combination, the two instruments have not heretofore been combined in a single unit.

SUMMARY OF THE INVENTION

In accordance with the present invention, a single unit as adapted for use with a microdermabrasion handpiece as well as an endermologie handpiece. A stream of air is controlled by a 3-way valve which alternatively directs the air along a first air stream to the microdermabrasion handpiece or a second air stream to the endermologie handpiece. The first air stream is directed through a source of crystals which are introduced into the first air stream to provide a flow of crystals which is then sent to the microdermabrasion handpiece. With the advent of a single unit, the mere selection of the 3-way valve permits the unit to be used for both microdermabrasion techniques and endermnologie techniques. This advantage is of particular interest because the microdermabrasion technique can be facilitated by the suction and massage associated with the endermologie technique.

Further control over the degree of abrasion can be provided by a valve which bypasses the source of crystals. A reduction in the amount of air flowing through the source of crystals reduces the crystal density without necessarily affecting the crystal velocity at the handpiece.

At the source of crystals, the first air stream is directed through a tube which is provided with a hole in communication with the crystals. This hole is sized and configured to limit the amount of crystals which can flow into the first air stream. Accordingly, the hole can be sized to control the crystal density by limiting the amount of crystals which can be introduced into a given volume of air. A larger hole results in a higher crystal density. Using this structure in combination with a bypass valve is of significant advantage in maximizing control over the crystal velocity density, and hence the degree of skin abrasion.

In the microdermabrasion handpiece, the abrasion window is positioned along the cap so that it is disposed between the supply path and the return path of the crystals. In a particular environment, the nozzle is positioned to direct the flow of crystals directly into the abrasion window of the cap. This seems to provide the greatest control over the skin abrasion process. It has been found that rectangular holes can offer certain advantages over the circular holes of the past. In these embodiments, the long dimension of the rectangle is typically oriented generally parallel to a plane including the nozzle and the return orifice.

These and other features and advantages of the invention will become more apparent with a description of preferred embodiments and reference to the associated drawings.

DESCRIPTION OF THE DRAWINGS

FIG. 6a is front elevation view of an additional embodiment of the microdermabrasion handpiece cap;

FIG. 6b is a side view and axial cross-section of the cap illustrated in FIG. 6a;

FIG. 7a is a front elevation view of a further embodiment of the microdermabrasion handpiece cap;

FIG. 7b is a side view and axial cross-section of the cap illustrated in FIG. 7a;

FIG. 8 is a side elevation view of a set of endermologie massage handpieces each offering a different size in order to permit control over the magnitude of suction and the area of application;

FIG. 9 is a front elevation view of a crystal supply station and crystal return station associated with one embodiment of the present invention;

DESCRIPTION OF THE PREFERRED EMBODIMENTS AND BEST MODE OF THE INVENTION

Figure 1:
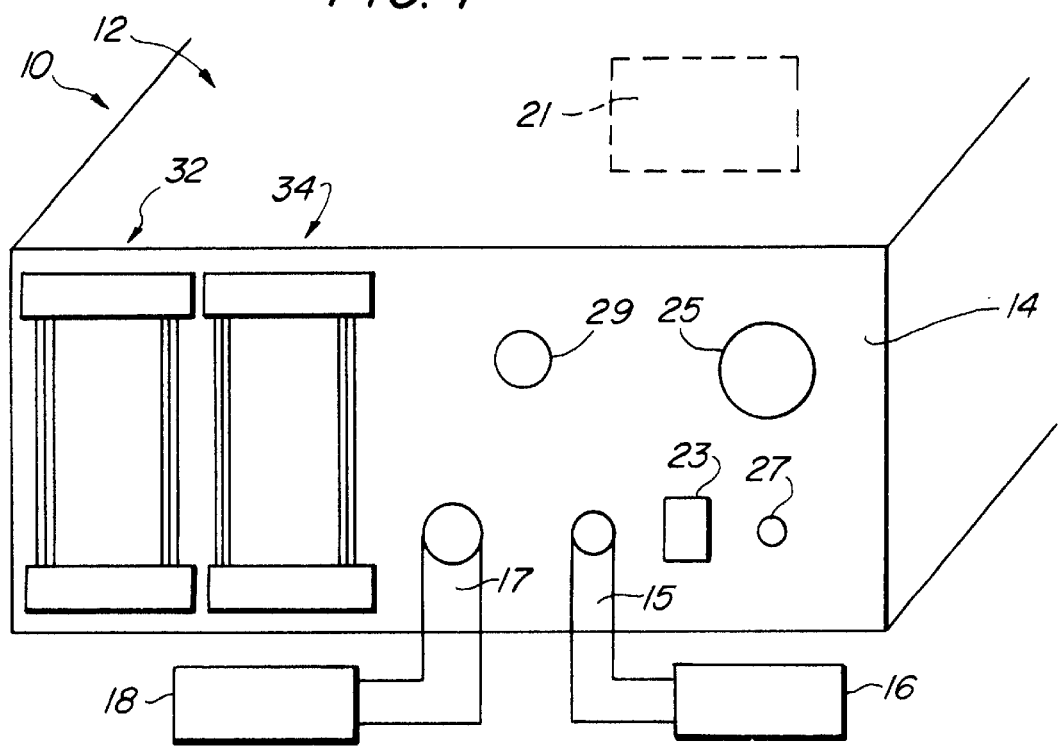
FIG. 1 is a perspective view of a microdermabrasion and endermologie apparatus of the present invention.

A preferred embodiment of the present invention is illustrated in FIG. 1 where a microdermabrasion and endermologie massage apparatus is designated by the reference numeral 10. The apparatus 10 includes a single housing 12 having a face plate 14 which is adapted for coupling through a flexible hose 15 to a microdermabrasion handpiece 16 and/or an endermologie handpiece 18. Enclosed within the single housing 12 is a single source of vacuum such as a vacuum pump 21. This pump 21 is activated by a power switch 23 and coupled through a vacuum gauge 25 and bleed valve 27 to a 3-way mode switch 29. The switch 29 is in turn coupled to the microdermabrasion handpiece 16 and endermologie handpiece 18. These coupling arrangements in a preferred embodiment are discussed in greater detail with reference to FIG. 2. A crystal supply station 32 and crystal return station 34 are disposed on the faceplate 14 of this embodiment.

Figure 2:
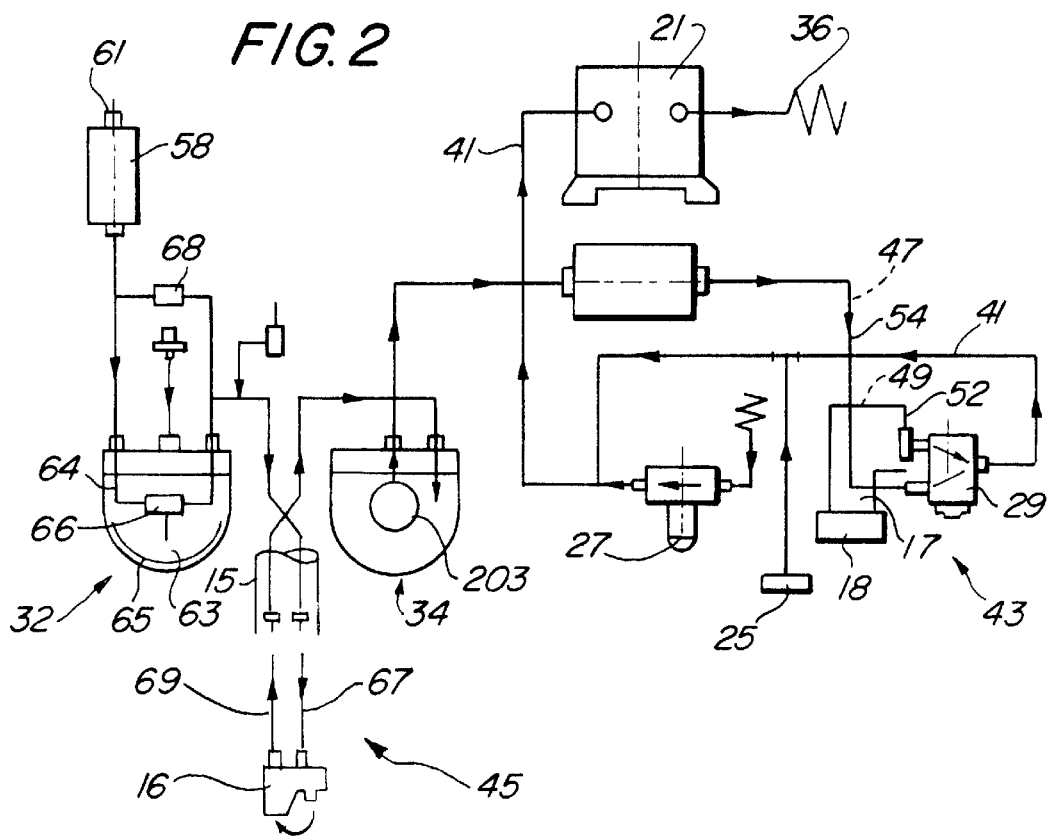
FIG. 2 is the schematic view of the apparatus illustrated in FIG. 1.

The vacuum pump 21 is illustrated schematically in FIG. 2 and provides motive power for the apparatus 10. The pump 21 has an exhaust 36 and power sufficient to pull a stream of air 38 through primary conduit 41. The magnitude of air pressure within the conduit 41 can be controlled by the bleed valve 27 which in the preferred embodiment is a needle valve.

As illustrated, the primary conduit 41 can be coupled to the 3-way valve or mode switch 29. By operation of this switch 29, suction can be applied alternatively to an endermologie suction 43 or a microdermabrasion section 45 of the apparatus 10. Thus the switch 29 can be used to divert the stream of air 38 alternatively to form a first air stream 49 in a secondary conduit 52 in the endermologie section 43, or alternatively to form a first stream of air 47 in a secondary conduit 54 in the microdermabrasion section 45, or alternatively a second stream of air 49 in a secondary conduit 52 in the endermologie section 43.

In the endermologie section 43 a second air stream 49 in a secondary conduit 52 provides suction at the handpiece 18. The first air stream 49 then passes back through the flexible hose 17 and into the mode switch 29 where the stream of air 38 is drawn through the primary conduit 41 by the vacuum pump 21.

Alternatively, the mode switch 29 can be set to draw the first air stream 47 through the conduit 54 in the microdermabrasion section 45. The conduit 54 is in turn coupled through HEPA filters 56, the crystal return station 34, the crystal supply station 32 and a second HEPA filter 58. The filter 58 in this case provides an air inlet 61 to the microdermabrasion section 45.

A supply of crystals 63 is disposed at the crystal supply station 32 where the secondary conduit 54 is connected to a pick-up tube 64 in a canister 65. In a manner discussed in greater detail below, the pick-up tube 64 can be provided with a crystal pick-up 66 which extends into the crystals 63 within the canister 65. In this manner a flow of the crystal 63 can be provided in the first air stream 47 as it is introduced through a supply lumen 67 in the flexible hose 15. The supply lumen 67 in turn introduces the flow of crystals 63 to the microdermabrasion handpiece 16 which is adapted to be held by the surgeon or technician and applied to the skin of the patient.

Of particular interest in the crystal supply station 32 is a bypass valve 68 which extends between the HEPA filter 58 and the supply lumen 67 of the handpiece 16. Thus the bypass valve 68 effectively extends across the inlet and the outlet of the crystal supply station 32. When the bypass valve 68 is open, suction is applied directly to the filter 68 and a portion of the air which would otherwise be input to the crystal supply station 32 is diverted to the output of the crystal supply station 32. As a result, the flow of air in the pickup tube 64 is decreased and the volume of crystals introduced into the crystal pickup 67 is commensurately reduced. At the output of the crystal supply station 32, the bypass air is recombined with the air in the pickup tube 64 so that the velocity of air introduced to the handpiece 16 is substantially constant. However, with a decrease in the volume of crystals introduced into the pickup tube 64, the density of the crystals is reduced. Thus the bypass valve 68 provides a mechanism for varying the crystal density without significantly adjusting the crystal velocity.

The used crystals 63 can be removed from the handpiece 16 through a return lumen 69 in the flexible hose 15. This flow of crystals 63 from the handpiece 16 is directed into the crystal return station 34, which is discussed in greater detail below. The debris and used crystals are removed from the first air stream 47 at the return station 34, as the first air stream 47 is directed through the filters 56 and the conduit 54 to the 3-way valve or mode switch 29. This completes the microdermabrasion section 45 of the embodiment.

In operation, the microdermabrasion section 45 would be activated through the 3-way mode selection switch 29 to facilitate skin abrasion by way of the handpiece 16. At the completion of this procedure, or in a totally different procedure, the mode switch 29 could be moved to its alternate position thereby activating the endermologie section 43.

Figure 3:
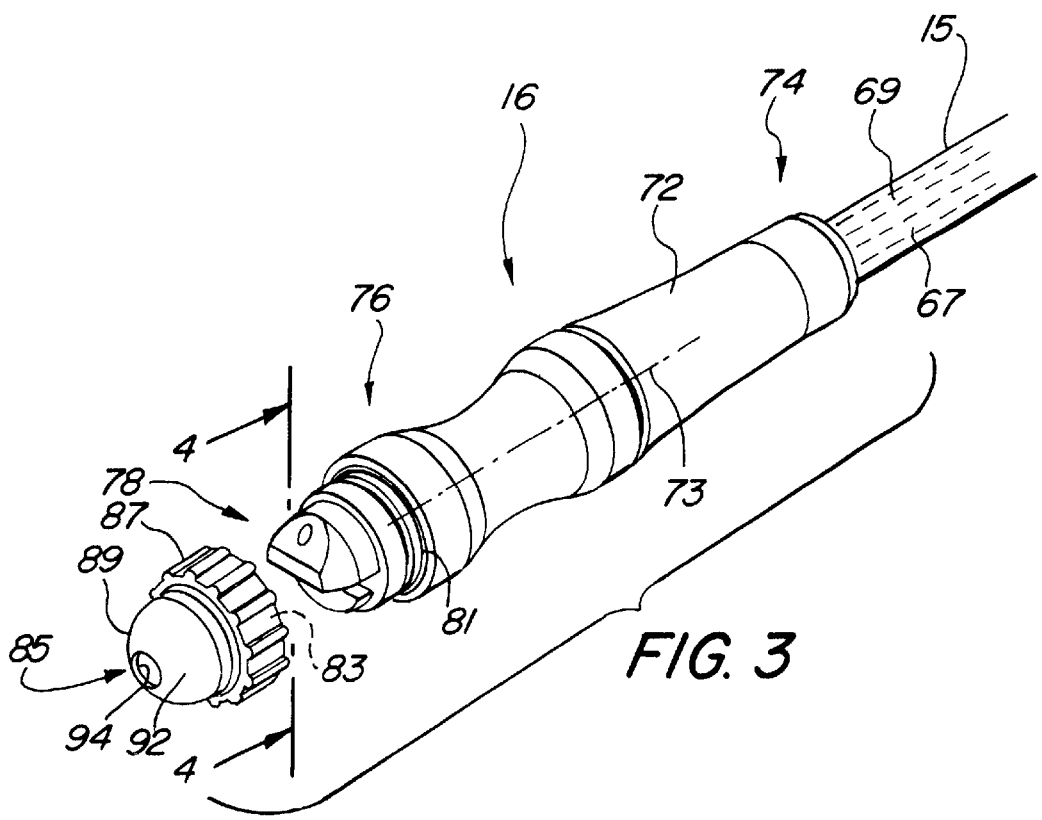
FIG. 3 is an exploded view of a microdermabrasion handpiece adapted for the apparatus of FIG. 1.

Given this operation of a preferred embodiment of the apparatus 10, details of the microdermabrasion handpiece 16 will now be discussed with reference to FIGS. 3–5. FIG. 3 is an exploded view showing a handle 72 having an axis 73 extending longitudinally between a proximal end 74 and a distal end 76. An air stream control device 78 is disposed at the distal end 76 of the handle 72 in fluid communication with the lumens 67 and 69 and the flexible hose 15. The device 78 can be provided with external threads 81 which register with internal threads 83 on a cap 85. Alternatively the cap 85 can be friction fit onto the device 78 to facilitate a proper orientation of these two structures. The cap 85 can be provided with a knurled circumference 87 and an end wall 89 which forms with the device 78 and abrasion chamber 92. An abrasion window 94 in the end wall 89 provides access to the abrasion chamber 92.

Figure 5:
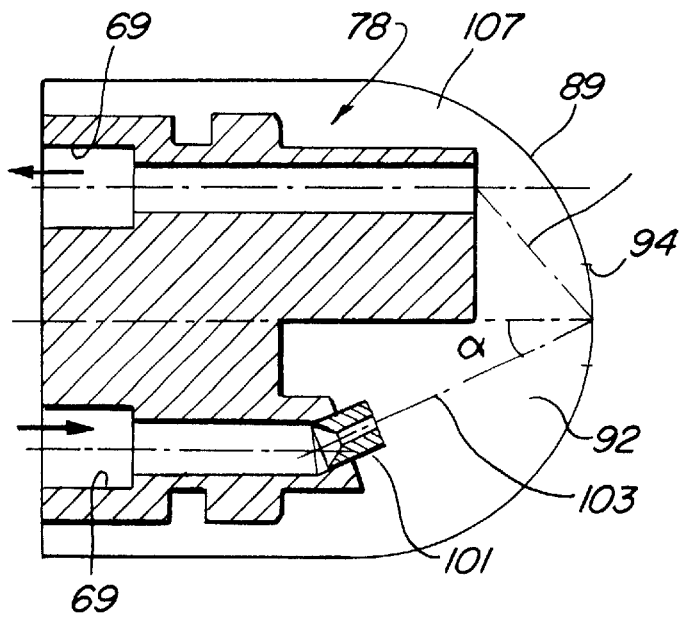
FIG. 5 is a cross-section view of the air control device (taken along lines 5—5 of FIG. 4.) and the associated cap.
Figure 4:
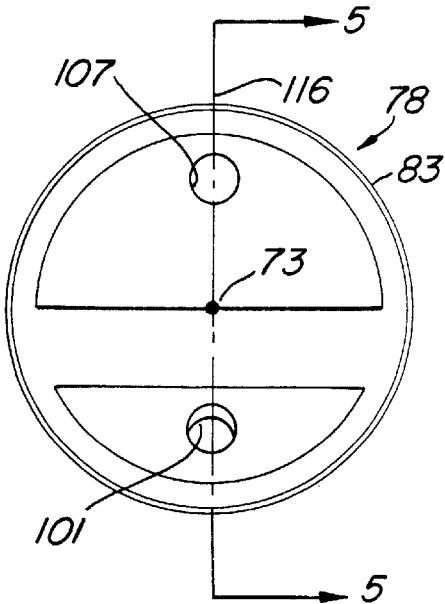
FIG. 4 is a front elevation view of an air control device associated with the handpiece of FIG. 3.

A preferred embodiment 86 of the air stream control device 78 is illustrated in greater detail in the front elevation view of FIG. 4 and the cross-section view of FIG. 5. From these views it can be seen that the device 78 can include a supply nozzle 101 which is disposed in fluid communication with the lumen 67 of the hose 15. The nozzle 101 receives the flow of crystals 63 from the supply lumen 67 and introduces that flow into the abrasion chamber 92. Importantly in this case, the nozzle 101 is positioned to direct the flow of crystals from the lumen 67 into the window 94. In an embodiment wherein the window 94 is disposed along the axis 73, and the lumen 67 is positioned in a parallel spaced relationship with the axis 73, the nozzle 101 is disposed at an angle a relative to the axis 73. Thus the flow of crystals 63 can be directed along a supply path 103 which has a distal component and an angle a relative to the axis 73. With the window 94 disposed at the distal most point of the end wall 89, the supply path 103 of this embodiment will always have a component in the distal direction.

After the flow of crystals 63 has abraded the patients skin through the window 94, the used crystals are then drawn along a return path 105 to an orifice 107 in the device 78. This orifice 107 is in fluid communication with the return lumen 69 of the hose 15 which sucks the crystals 63 into the hose 15 and from the hose 15 into the return station 34.

It will be noted that in the embodiment of FIG. 5, the window 94 has the configuration of a circle having its center disposed along the axis 73. Other shapes for the window 94 have been found particularly advantageous. In one such embodiment illustrated in FIGS. 6a and 6b, the window 94 has the configuration of a rectangle 109 having a long side 112. This window 109 is formed in an end wall 114 which has a generally planer configuration and is positioned at an angle to the axis 73. The window 109 is formed in the end wall 114 with its long side 112 disposed generally parallel to a plane 116 (FIG. 4) passing through the nozzle 101 and orifice 107.

In another embodiment illustrated in FIGS. 7a and 7b, a rectangular window 118 similar to the window 109 and having a long side 121 is disposed in an end wall 123. This end wall 123 has a generally planer configuration and is disposed generally perpendicular to the axis 73. Extending from the window 118, are opposing sidewalls 127 and 129 which extend proximally outwardly from the associated long sides of the window 118. For example, the sidewall 127 extends generally parallel to the long side 121 of the window 118. Both of the side walls 127 and 129 are disposed in respective planes 132 and 134 which are generally parallel to the long side 121 and have an angular relationship with the axis 73. In a preferred embodiment, the planes 132 and 134 of the sidewalls 27 and 29, respectfully, are generally perpendicular to each other.

FIG. 8 illustrates a set 141 of three endermologie handpieces 143, 145 and 147. Each of these handpieces is similar to the handpiece 18 illustrated in FIG. 1. Thus, the handpiece 143 includes a handle section 149 which typically has a cylindrical configuration and a diameter which is comfortable for the surgeon or technician to hold in his hand. An operative section 152 is disposed distally of the handle section 149 and provided with a finger hole 153. This operative section 152 may also have a cylindrical configuration but will typically have a diameter greater than that of the handle section 149. A conical transition section 154 can be disposed between the handle section 149 and the operative section 152. A suction window 156 at the distal end of the handpiece 143 will typically have a diameter equivalent to that of the operative section 152.

The handpieces 145 and 147 can be similar to the handpiece 143 in that they will typically include a handle section, such as the section 149, and an operative section, such as the section 152. In the case of these handpieces 145 and 147, the diameter of the handle sections may be equivalent to the diameter of the handle section 149. However, the operative sections of the handpieces 145 and 147 will typically have windows 146 and 148, respectively, with diameters different than that of the window 156 in operative section 152. Thus, the set 141 will offer the surgeon or technician a choice of handpieces 143, 145 and 147 each having a suction window, such as the window 156, of different diameters. By selecting a particular one of the handpieces 143–147, a different suction pressure and size of operative area can be chosen.

Another feature of the present invention is associated with the crystal supply station 32 and crystal return station 34. In an embodiment illustrated in FIG. 9, these stations 32 and 34 each include a bottom support 158 typically fixed to the face plate 14, and a top support 161 which is attached to posts 163 that extend through holes in the bottom support 158. Beneath the bottom support 158, the posts 163 are threaded, passed through associated springs 165, and terminated in associated nuts 167. Since the top support 161 is typically not fixed to the faceplate 14, it can be biased by the springs 165 from an extended relationship to a closely spaced relationship with the bottom support 158. This structure enables the top support 161 to be moved upwardly to the extended relationship thereby permitting insertion of the canister 65 of crystals 63. Once the canister 65 is installed, the top support 161 can be released permitting the springs 165 to bias the top support 161 into the closely spaced relationship with the bottom support 158, thereby capturing the canister 65.

As previously discussed with referenced FIG. 2, the first air stream can be introduced through the pick-up tube 64 which extends into the crystals 63 within the canister 65. This tube 64 will typically have a U-shaped configuration thereby permitting accommodating both ends of the tubes 64 to extend through the top support 161 while allowing an intermediate section of the tube 64 to be deeply embedded the crystal 63. The crystal pick-up 66 is preferably disposed in this intermediate section 183 near the bottom of the canister 65. In a preferred embodiment, the pick up 66 is formed as a hole in the wall of the tube 64 thereby providing access for the crystals 63 into the first air stream 47 in the tube 64. The hole 66 can be carefully sized to control the amount of crystals introduced into the tube 64 per unit volume of the first air stream 47. The larger the hole 66, the greater the amount of crystal introduced into the stream and therefore the higher the crystal density within the first air stream. The smaller the hole the less the crystal density in the first air stream. Variations in the size of the hole 66 can be provided by removable plugs or adhesive patches associated with the intermediate section 183.

The crystal return station 34 can be constructed in a manner similar to that of the crystal supply station 32 except that the input to the station 34 is provided by an inlet tube 184 in communication with the return lumen 69 from the tube 15, and an exit tube 186 in communication with secondary conduit 54 the first air stream 47. Otherwise, the bottom support 169, top support 172, post 174, springs 176 and nuts 178 can function in the manner previously discussed to permit the removable insertion of the canister 181.

The canister 181 can be provided with an O-ring 187 which defines an inlet hole 189 into the canister 181. This O-ring 187 forms a seal with the inlet tube 184, which is in fluid communication with the return lumen 69 of the handpiece 16. A downspout 192 extends from the O-ring 187 into proximity with the opposite end of the canister 181.

As the debris and used crystals 63 exit the handpiece 16, they travel along the return lumen 69 and the inlet tube 184 to the return station 32, where they pass through the downspout 192 and are collected in the canister 181. In an exit passage, clean air is provided to the secondary conduit 54 which extends through a hole 196 defined by an O-ring 198 disposed in the top of the canister 181. Attached to the O-ring 198 is a filter 203 which is preferably pleated and may be formed of paper or fabric.

The filter 203 provides filtration of the air exiting the crystal return station 34 into the conduit 54. Since this exit air forms the first air stream which in turn must pass through the 3-way mode selector valve 29 and the vacuum pump 21, it is important that the crystals 63, and any fragments thereof, be removed by this exit filter 203.

When the canister 181 is full, it can be removed by elevating the top support 172 against the bias of the springs 176 and withdrawing the canister 181 and its O-rings 187 and 196 from the associated tubes 184 and 186. The full canister 181 can then be discarded and replaced with an empty canister 181. Alternatively, the canister 181 can be made non-disposable and provided with a drain tube 188 and removable hemostat 190. This configuration will enable the contents of the canister 181 to be removed through the drain 188 and collected in a biologically hazardous bag. A similar drain and hemostat can be used with a non-disposable canister 65 in the crystal supply station 32. This configuration will enable various grit sizes to be changed through the associated drain.

Another feature of the present invention accommodates the need for back flushing all or various components of the system under certain circumstances. For example, if one of the crystals 63 becomes lodged in the hole 66 of the pickup tube 64, it may be desirable to blow air in a reverse direction through the crystal supply station 32. Realizing that the vacuum pump 21 will typically have an output of pressurized fluid, these and similar circumstances can be accommodated by connecting various components of the system to the output of the vacuum pump 21. The pressurized air available at this location would then be introduced into the system in a reverse direction to back flush various components. In the example noted, the output of the crystal supply station 32 could be connected to the output of the vacuum pump 21 to back flush the hole 66 and dislodge any crystals. Other components of the system which might be connected to the output of the vacuum pump 21 might include for example the conduit 41 as well as the conduits 52 and 54, the return lumen 69 of the handpiece 16, or the exit tube 186.

Figure 10:
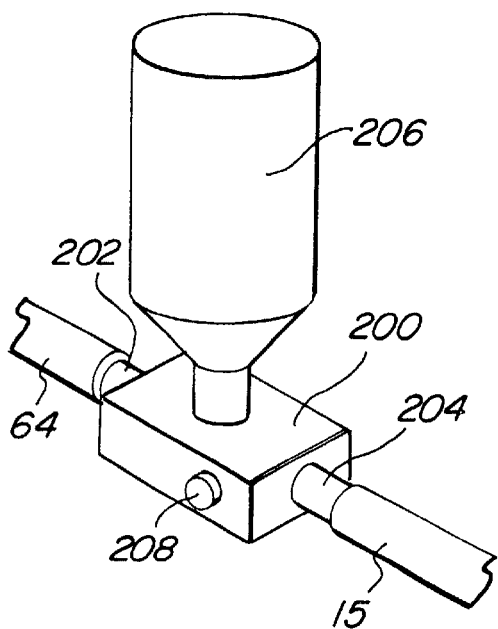
FIG. 10 is a perspective view of a further embodiment of a crystal pick-up station.

A further embodiment of the invention illustrated in FIG. 10 is characterized by a crystal supply station 32 which is slightly different than the embodiments described with reference to FIGS. 1 and 9. In this case, the crystal supply station 32 is disposed between the pick-up tube 64 and the flexible hose 15 which provides the supply lumen 7 to the handpiece 16 (FIG. 2). In this case, a support block 200 is provided with an input connector 202 and an output connector 204 which are adapted for connection to the pick-up tube 64 and flexible hose 15, respectively. The block 200 can be mounted in a fixed relationship to the face plate 14 (FIG. 1) or adapted to stand alone in a spaced relationship with the housing 12. In either case, the block 200 is adapted to support a container of the crystals such as a plastic bottle 206 as illustrated in FIG. 10. The container or bottle 206 can be inverted and attached to the block 200 in order to provide a gravity feed of the crystals into the block 200. Air passing from the tube 64 into the hose 15 picks up the crystals from the support block 200 in an amount controllable by an adjustment knob 208.

Figure 11:
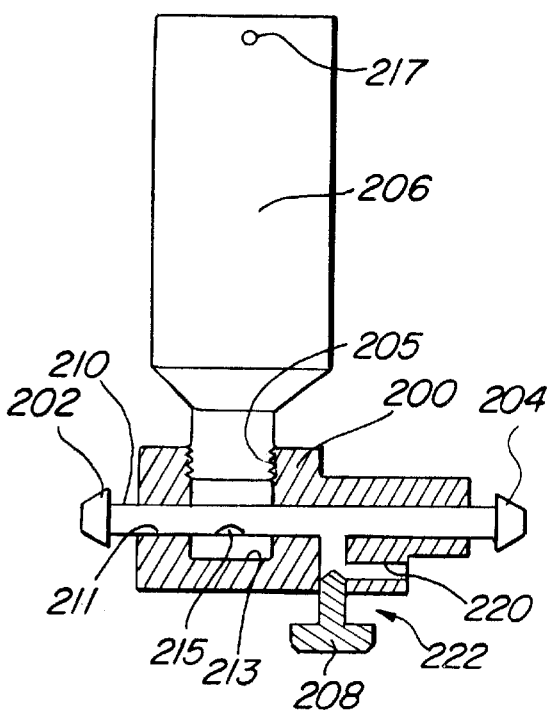
FIG. 11 is an axial cross-section view of the crystal pick-up station illustrated in FIG. 10.

The operation of this crystal supply station 32 can be better understood with reference to the cross-section view of FIG. 11. In this view it can be seen that a tube 210 forms a channel 211 which provides fluid communication between the inlet connector 202 and the outlet connector 204. This tube 210 extends through a cavity 213 in the block 200 which in turn communicates with the interior regions of the container or bottle 206. A hole 215 in the tube 210 provides communication between the cavity 213 and the channel 211. In operation, the bottle 206 is inverted and attached to the block 200. This attachment can be facilitated by a screw thread, a bayonet connection, or a snap fit. In any case, it is preferable that the attachment form a seal between the bottle 206 and the block 200. With a gravity flow of crystals from the bottle 206 into the cavity 213, a constant supply of the crystals is provided at the hole 215. This gravity flow can be facilitated by providing an air hole 217 at the opposite end of the bottle 206. As air flows from the inlet connector 202 through the channel 211, it creates a Venturi effect at the hole 215 drawing crystals through the hole 215 into the channel 211.

In a preferred embodiment, the channel 211 is accessed through a bypass conduit 220 which provides bypass air in an amount dependent upon adjustment of a needle valve 222 and associated adjustment knob 208. At the junction of the channel 211 and the bypass conduit 220, a constant supply of the crystals is provided. As the bypass air is increased through the conduit 220, the ratio of crystals to air at the outlet conduit 204 is decreased. Similarly, if the bypass air is decreased by adjustment of the knob 208, the ratio of crystals to air is increased at the outlet connector 204. Thus, by merely adjusting the knob 208, the concentration of crystals within the airflow can be controlled by the user.

Figure 12:
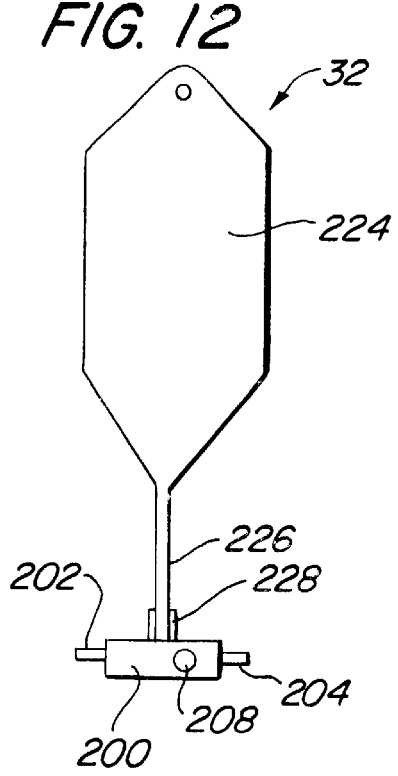
FIG. 12 is a side elevational view of an additional embodiment of the crystal pick-up station.

An additional embodiment of the crystal supply station 32 is illustrated in FIG. 12. In this case the crystals are supplied in a flexible plastic bag 224 which provides a gravity flow of the crystals through tubing 226. A special connector 228 is provided on the block 200 in this embodiment, in order to form a seal between the block 200 and the tubing 226.

Figure 13:
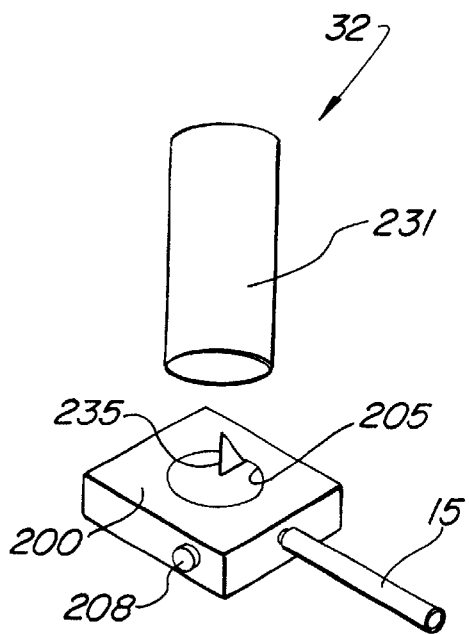
FIG. 13 is a perspective view of still a further embodiment of the crystal pick-up station.

In still a further embodiment illustrated in FIG. 13, the crystals can be provided in a disposable container such as a cartridge 231. In this case, the cartridge 231 is provided as a disposable item with the crystals sealed within the cartridge 231 by a puncturable membrane 233. In this particular embodiment, the block 200 can be provided with canister mounting hole 205 and a blade 235 or other puncturing device mounted within the hole 205. In operation, the canister 231 can be brought into engagement with the block 200 at the mounting hole 205. In this mounting step, the blade 235 will puncture the membrane 233 releasing the crystals from the cartridge 231 into the cavity 213 (FIG. 11). Once the crystals are within the cavity 213, operation of the support block 200 can proceed in the manner discussed with reference to FIG. 11.

With a broader view of the entire apparatus illustrated in FIG. 2, it will be appreciated that the microdermabrasion section 45 and endermologie section 43 can be combined in a single unit and operated from a single vacuum source and mode selector switch. Only a single unit need be purchased by the surgeon or technician in order to perform both functions. This will be particularly appreciated in those procedures where the microdermabrasion process is facilitated by suction massage.

Providing for pick up of the crystals 63 through the hole 66 directly into the tube 64 is of particular advantage and permits control over the crystal density with an appropriate choice of diameter for the crystal pick-up hole 185. In addition, the provision of separate valves 27 and 68 in the microdermabrasion section 45, greatly increases the control over crystal density and velocity. Where the bleed valve 27 controls crystal velocity but not crystal density, the bypass valve 68 controls crystal density but not crystal velocity.

Given these wide variations, which are all within the scope of this concept, one is cautioned not to restrict the invention to the embodiments which have been specifically disclosed and illustrated, but rather encouraged to determine the scope of the invention only with reference to the following claims.

What is claimed is:

1. A microdermabrasion apparatus adapted to abrade skin of a patient, including:
    a handpiece adapted to be moved over the skin of the patient;
    a grit supply station providing a fluid flow containing a grit, the grit being projected against the skin to abrade the skin;
    a grit return station adapted to receive the fluid flow and the used grit with particles of the abraded skin;
    a support block included in the grit supply station;
    first portions of the support block defining a cavity in communication with the fluid flow; and
    second portions of the support block adapted to removably receive a container of the grit in a gravity flow relationship, the second portions of the support block communicating with the first portions of the support block to introduce the grit to the cavity.

2. The microdermabrasion apparatus recited in claim 1 wherein the grit supply station includes a container of the grit supported by the support block.

3. The microdermabrasion apparatus recited in claim 2 wherein the container of grit is a bottle having a substantially rigid wall with portions of the bottle defining an air relief hole.

4. The microdermabrasion apparatus recited in claim 2 wherein the container of grit includes a bag having a flexible wall.

5. The microdermabrasion apparatus recited in claim 2 wherein the container of grit includes a canister having a wall sealed by a puncturable membrane.

6. The microdermabrasion apparatus recited in claim 5 wherein the second portions of the support block define an opening into the support block, and the apparatus further comprises:
    a puncture element positioned within the opening in the support block to puncture the membrane of the canister.

7. The microdermabrasion apparatus recited in claim 1, further comprising:
    a flow channel defined in the support block and adapted for receiving the fluid flow; and
    a bypass lumen formed in the support block and providing an adjustable flow of bypass air into the flow channel to control the density of the grit in the fluid flow.

8. The microdermabrasion apparatus recited in claim 7 further comprising:
    an air bypass lumen formed in the support block in fluid communication with the flow channel;
    an adjustment knob carried by the block and accessible from outside the block, the adjustment knob extending into the air bypass lumen a distance adjustable to control the density of the grit in the fluid flow.

9. The microdermabrasion apparatus adapted to abrade skin of a patient, including:
    a handpiece adapted to be moved over the skin of the patient;
    grit supply station coupled to the handpiece and providing a fluid flow containing a grit, the grit being adapted to contact the skin to abrade the skin;
    a grit return station adapted to receive the fluid flow and the used grit with particles of the abraded skin;
    a support block included in the grit supply station and adapted to receive the fluid flow in a flow channel;
    first portions of the support block defining a cavity in fluid communication with the flow channel, the cavity being adapted to removably receive a supply of the grit; and second portions of the support block defining an air bypass lumen providing an adjustable flow of bypass air into the flow channel to control the density of grit in the fluid flow.

10. The microdermabrasion apparatus recited in claim 9, wherein:

the cavity has an inlet side and an outlet side; and the lumen is in fluid communication with the flow channel on the outlet side of the cavity.

11. The microdermabrasion apparatus recited in claim 10, further comprising:

an adjustment knob carried by the support block and accessible from outside the support block, the adjustment knob extending into the air bypass lumen a distance adjustable to control the density of the grit in the fluid flow.

12. The microdermabrasion apparatus recited in claim 9, wherein the first portions of the support block define an opening into the cavity and the apparatus further comprises:

a container of the grit disposed in gravity flow communication through the opening with the cavity to provide a supply of grit to the cavity.

13. The microdermabrasion apparatus recited in claim 12, wherein:

the container includes a puncturable membrane; and the support block includes a puncturing element extending through the opening and adapted to puncture the membrane of the container when the container is mounted on the support block.

14. A method for providing a flow of grit in a microdermabrasion apparatus, comprising the steps of:

providing a grit supply station with a support block having a cavity in fluid communication with a flow channel;

mounting a container of grit on the support block in fluid communication with the cavity;

introducing a fluid flow into the flow channel;

providing a gravity flow of the grit from the container into the cavity; and drawing a portion of the grit from the cavity into the fluid flow to provide a flow of the grit.

15. The method recited in claim 14, wherein the mounting step includes the step of inverting the container to provide a gravity flow of the grit into the cavity.

16. The method recited in claim 14, wherein the mounting step includes the steps of:

providing the container with substantially rigid walls; and forming an air relief hole in the wall of the container.

17. The method recited in claim 14, wherein the mounting step includes the step of providing the container with a substantially flexible wall.

18. The method recited in claim 14, wherein the mounting step includes the steps of:

providing the container with a puncturable membrane; and puncturing the membrane to provide a gravity flow of the grit into the container.

19. The microdermabrasion apparatus recited in claim 1 wherein the support block further comprises a tube adapted for receiving the fluid flow, the tube defining a hole in communication with the cavity.

* * * * *